United States Patent

Wuest et al.

Patent Number: 4,918,212
Date of Patent: Apr. 17, 1990

[54] ARYLPHOSPHORUS DERIVATIVES

[75] Inventors: Hans-Heiner Wuest, Dossenheim; Bernd Janssen, Ludwigshafen, both of Fed. Rep. of Germany

[73] Assignee: BASF Aktiengesellschaft, Ludwigshafen, Fed. Rep. of Germany

[21] Appl. No.: 231,475

[22] Filed: Aug. 12, 1988

[30] Foreign Application Priority Data

Aug. 12, 1987 [DE] Fed. Rep. of Germany ....... 3726806

[51] Int. Cl.⁴ ............................. C07F 9/38; C07F 9/40
[52] U.S. Cl. ......................................... 558/214; 562/8
[58] Field of Search ............................. 558/214; 562/8

[56] References Cited

FOREIGN PATENT DOCUMENTS 2854354 7/1979 Fed. Rep. of Germany.
3202118 7/1983 Fed. Rep. of Germany.

*Primary Examiner*—Anton H. Sutto
*Attorney, Agent, or Firm*—Oblon, Spivak, McClelland, Maier & Neustadt

[57] ABSTRACT

Phosphonic acid, phosphinic acid and phosphine oxide derivatives of the general formula

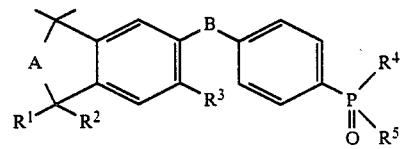

where A, B and $R^1$ to $R^5$ have the meanings stated in the description, processes for their preparation, pharmaceutical agents containing them, and their use for the treatment of acne and psoriasis are described.

7 Claims, No Drawings

ARYLPHOSPHORUS DERIVATIVES

The present invention relates to novel phosphonic acid, phosphinic acid and phosphine oxide derivatives, processes for their preparation and their use in the treatment of dermatological diseases.

German Laid-Open Applications Nos. DOS 2,854,354 and DOS 3,202,118 disclose that retinoidal benzoic acid derivatives have pharmacological actions in the topical and systemic therapy of neoplasias and dermatoses, for example acne or psoriasis. A disadvantage of these compounds is their small therapeutic index with regard to the side effects summarized under the term hypervitaminosis A.

We have found that arylphosphorus derivatives of the general formula

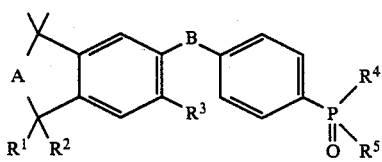
I where A is an unsubstituted or methyl-substituted ethylene or methylene radical, B is a —CR$^6$=CH— or —C≡C— group, R$^1$ and R$^2$ are each hydrogen or methyl, R$^3$ is hydrogen, C$_1$-C$_4$-alkyl, halogen, preferably fluorine, or methoxy and R$^4$ and R$^5$ are each C$_1$-C$_6$-alkyl, phenyl, a radical —OR$^7$ or —NR$^8$R$^9$, R$^6$ is hydrogen or C$_1$-C$_4$-alkyl, R$^7$, R$^8$ and R$^9$ are each hydrogen, an unsubstituted or hydroxyl-substituted C$_1$-C$_4$-radical or phenyl, where two hetero atoms bonded to phosphorus may be linked by a C$_2$- or C$_3$-alkylene group, or, together with the nitrogen atom to which they are bonded, form a heterocyclic radical, preferably a morpholine, pyrrolidine or piperidine radical, and their physiologically tolerated salts have an improved profile of action, especially with regard to the side effects.

The novel compounds can be prepared by a process in which (a) an aldehyde or a ketone of the formula II

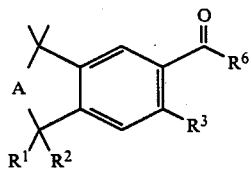
II where R$^1$, R$^2$, R$^3$, R$^6$ and A have the abovementioned meanings, is subjected to a Wittig-Horner reaction with a phosphonate of the formula III

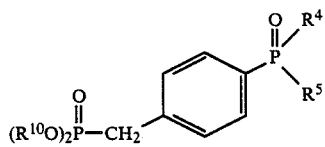
III where R$^4$ and R$^5$ have the abovementioned meanings and R$^{10}$ is C$_1$-C$_4$-alkyl, or (b) a phosphonium compound of the formula IV

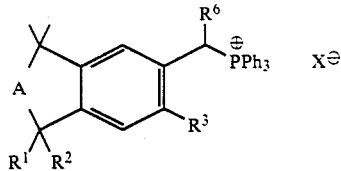
IV where R$^1$, R$^2$, R$^3$, R$^6$ and A have the abovementioned meanings and X is an inorganic anion, is subjected to a Wittig reaction with an aldehyde of the formula V

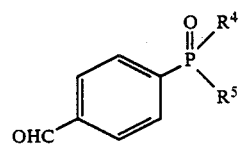
V where R$^4$ and R$^5$ have the abovementioned meanings, or (c) an aryl halide of the formula VI

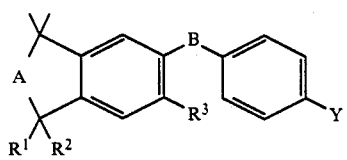
VI where R$^1$, R$^2$, R$^3$, A and B have the abovementioned meanings and Y is halogen, is reacted with a phosphorus compound of the formula VII

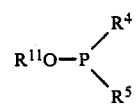
VII where R$^4$ and R$^5$ have the abovementioned meanings and R$^{11}$ is C$_1$-C$_6$-alkyl, advantageously in the presence of a transition metal catalyst, or (d) an arylacetylene of the formula VIII

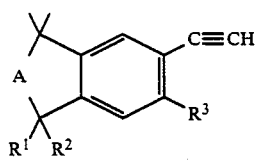
VIII where R$^1$, R$^2$, R$^3$ and A have the abovementioned meanings, is reacted with an aryl halide of the formula IX

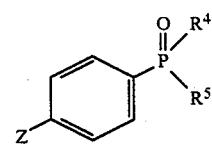
IX where R$^4$ and R$^5$ have the abovementioned meanings and Y is halogen, advantageously in the presence of a transition metal catalyst, and, if required, (e) the compound obtained in processes (a)–(c) is converted into another compound of the formula I by a standard method.

The halogen atoms Y in (c) and Z in (d) are preferably bromine or iodine.

The Wittig-Horner and Wittig reactions in (a) and (b) take place at up to 100° C., advantageously from 20° to 50° C. The reaction may be carried out under atmospheric pressure or in a closed vessel under superatmospheric pressure.

This reaction can be carried out in the presence of a diluent or solvent, for example a lower saturated dialkyl ether, dialkylglycol ether or cyclic ether, such as diethyl ether, ethyl tert-butyl ether, 1,2-dimethoxyethane, tetrahydrofuran or dioxane, an aromatic hydrocarbon, such as benzene, toluene or xylene, or a saturated aliphatic hydrocarbon, such as hexane, heptane or isooctane, a dialkylformamide or dialkyl sulfoxide, such as dimethylformamide or dimethyl sulfoxide, or in a mixture of the stated solvents. A cyclic ether, such as tetrahydrofuran, or, in particular, dimethylformamide or dimethyl sulfoxide or a mixture of these is preferably used, the reaction generally taking place at up to 30° C.

The Wittig and Wittig-Horner reactions are carried out in the presence of a deprotonating agent for the phosphonate II or the phosphonium salt IV. Suitable compounds are alkali metal hydrides and alkali metal amides, in particular those of sodium and those of potassium, the sodium and potassium salts of dimethyl sulfoxide, alkyllithium compounds, such as n-butyllithium, or alkali metal alcoholates, preferably sodium ethylate, sodium methylate or potassium tert-butylate.

The Wittig or Wittig-Horner reaction usually gives a mixture of the sterically isomeric (E/Z) olefins.

E/Z isomer mixtures containing a predominant proportion of the Z isomer are isomerized at the olefinic double bond under the action of light and/or with the addition of a catalytic amount of iodine to give a mixture having a higher content of the E isomer. A pure (E) compound of the formula I is then advantageously obtained from the resulting (E/Z)-isomer mixture which now has a more favorable (E) content, preferably by crystallization or a chromatographic method, such as column chromatography or preparative HPLC.

The reaction in (c), particularly when Y in formula VI is chlorine or bromine, as well as when Y is iodine, is advantageously catalyzed by a transition metal catalyst, for example copper powder, salts or complexes of nickel or of palladium, preferably nickel(II) chloride or nickel(II) bromide. The reaction is carried out at from 100° to 200° C., preferably from 120° to 160° C.

It is possible to add a solvent, for example an aromatic hydrocarbon, such as toluene or xylene.

In reaction (d), the corresponding copper acetylides are prepared in situ in a conventional manner from compounds of the formula VIII and are further reacted with the aryl halides IX to give compounds of the formula I. Alternatively, the coupling reaction, starting directly from acetylenes VIII, can be catalyzed by complexes of palladium and of nickel, for example with triphenylphosphine. In every case, the presence of a base is advantageous, for example an organic nitrogen base, such as triethylamine or pyridine, or an alkali metal alcoholate, such as sodium methylate or sodium phenolate. If necessary, the reaction is carried out in a solvent, preferably in dimethylformamide or tetrahydrofuran. The reaction takes place at from 40° to 150° C., advantageously at about 50° C. (aryl iodides) or about 100° C. (aryl bromides).

Re (e):

By hydrolysis of the phosphonic diesters and phosphinic esters of the formula I in a conventional manner, it is possible, to prepare the phosphonic and phosphinic acids or phosphonic monoesters, depending on the choice of hydrolysis conditions. Hydrolysis of the phosphonic diesters with aqueous hydroxides of alkali metals and alkaline earth metals, preferably sodium hydroxide or potassium hydroxide, generally leads to the corresponding phosphonic monoesters. Complete hydrolysis is effected by reacting the phosphonic diesters with trialkylhalosilanes, preferably trimethylbromosilane or trimethyliodosilane, which are advantageously prepared in situ from trimethylchlorosilane and an alkali metal bromide or iodide, and then treating the product with water or a dilute mineral acid, e.g. hydrochloric acid or sulfuric acid.

Further novel compounds can be prepared from the resulting acids by known procedures. For example, a phosphonic acid of the formula I can be converted, for example with phosphorus pentachloride, into the phosphonyl dichloride, which is reacted with an alcohol or an amine to give the corresponding ester or amide, respectively.

Phosphonic esters, phosphinic esters, phosphonyl chlorides or phosphinyl chlorides can be reacted with organometallic reagents, for example Grignard compounds, to give corresponding phosphine oxide derivatives.

Because of their pharmacological properties, the compounds according to the invention and their physiologically tolerated salts can be used in the topical and systemic therapy of acne, psoriasis and other dermatological diseases accompanied by pathologically changed cornification.

The dermatological activity, for example in the treatment of acne, can be demonstrated, inter alia, by the comedolytic activity and the ability to reduce the number of cysts in the rhino mouse model. This method is described by L. H. Kligman et al. in The Journal of Investigative Dermatology 73 (1978), 354–358.

Accordingly, the present invention furthermore relates to therapeutic agents for topical and systemic use against acne and psoriasis, the said agents containing a compound of the formula (I) as the active compound in addition to conventional carriers or diluents, and the preparation of a drug of this type using a compound of the formula (I) as the active compound.

The therapeutic agents or formulations are prepared in a conventional manner using the usual liquid or solid carriers or diluents and the conventional pharmaceutical auxiliaries, in accordance with the desired route of administration and in a dose suitable for administration, for example by mixing the active compound with the solid or liquid carriers and auxiliaries usually used in such preparations.

Accordingly, the agents can be administered perorally, parenterally or topically. Formulations of this type are, for example, tablets, film tablets, coated tablets, capsules, pills, powders, solutions or suspensions, infusion or injection solutions and pastes, ointments, gels, creams, lotions, powders, solutions or emulsions and sprays.

The therapeutic agents may contain the compounds to be used according to the invention in a concentration of from 0.0001 to 1, preferably from 0.001 to 0.1, % in the case of topical administration and preferably in a single dose of from 0.1 to 50 mg per kg body weight in the case of systemic administration, and may be administered daily in one or more doses, depending on the nature and severity of the diseases.

Conventionally used pharmaceutical auxiliaries are, for example, alcohols, such as ethanol or isopropanol, oxyethylated castor oil or oxyethylated hydrogenated castor oil, polyacrylic acid, glycerol monostearate, liquid paraffin, vaseline, wool fat, polyethylene glycol 400, polyethylene glycol 400 stearate and oxyethylated fatty alcohols for topical administration and lactose, propylene glycol, ethanol, starch, talc or polyvinyl pyrrolidone for systemic use. If necessary, an antioxidant, e.g. tocopherol, and butylated hydroxyanisole or butylated hydroxytoluene or flavor improvers, stabilizers, emulsifiers, bleaches, etc. may be added to the preparations. A precondition is that all substances used in the preparation of pharmaceutical formulations are toxicologically acceptable and compatible with the active compounds used.

Some of the novel compounds have an acidic hydrogen atom and can therefore be converted into a physiologically tolerated, readily water-soluble salt with a base in a conventional manner. Examples of suitable salts are ammonium and alkali metal salts, in particular those of sodium, of potassium and of lithium, and alkaline earth metal salts, in particular those of calcium or of magnesium, and salts with suitable organic bases, such as those with lower alkylamines, e.g. methylamine, ethylamine or cyclohexylamine, or with substituted lower alkylamines, in particular hydroxyl-substituted alkylamines, such as diethanolamine, triethanolamine or tris-(hydroxymethyl)aminomethane, and with piperidine or morpholine.

Preparation of the compounds according to the invention

EXAMPLE 1

Diethyl (E)-4-[2-(5,6,7,8-tetrahydro-5,5,8,8-tetramethyl-2-naphthyl)-1-propenyl]-benzenephosphonate 20 g (52 millimoles) of (E)-1-(4-bromophenyl)-2-(5,6,7,8-tetrahydro-5,5,8,8-tetramethyl-2-naphthyl)-1-propene and 0.86 g (7.5 mol %) of anhydrous nickel(II) bromide were heated to about 160° C. under nitrogen in a distillation apparatus equipped with a dropping funnel. 104 g (60 millimoles) of triethyl phosphite were then added dropwise in such a way that the rate of dropwise addition corresponded to the rate at which the ethyl bromide distilled off. Stirring was continued for 0.5 hour, after which the mixture was cooled, a little toluene was added and the mixture was evaporated down. The residue was filtered with ethyl acetate over silica gel. 14.2 g (62%) of the title compound of melting point 72.5°-73.5° C. (from heptane) were obtained in this manner. Preparation of 1-(bromophenyl)-2-(5,6,7,8-tetrahydro-5,5,8,8-tetramethyl-2-naphthyl)-1-propene A solution of 30.7 g (0.1 mole) of diethyl 4-bromobenzylphosphonate in 50 ml of dimethyl sulfoxide was added dropwise at room temperature to a suspension of 2.4 g (0.1 mole) of sodium hydride in 100 ml of dry dimethyl sulfoxide. Stirring was continued for 1 hour, after which a solution of 17.3 g (0.075 mole) of 2-acetyl-5,6,7,8-tetrahydro-5,5,8,8-tetramethylnaphthalene in 25 ml of dimethyl sulfoxide were added dropwise.

Stirring was continued for 16 hours at room temperature, the mixture was poured onto 1 l of water and the resulting precipitate was filtered off under suction. It was washed with water and then with methanol and dried to give 5.7 g of 1-(bromophenyl)-2-(5,6,7,8-tetrahydro-5,5,8,8-tetramethyl-2-naphthyl)-1-propene of melting point 116°-117° C.

EXAMPLES 2-6

The compounds in Table 1 below were prepared similarly to Example 1.

TABLE 1

| Example | Name | A | $R^1$ | $R^2$ | $R^3$ | B | $R^4$ | $R^5$ | mp. (°C.) |
|---|---|---|---|---|---|---|---|---|---|
| 2 | Dimethyl (E)-4-[2-(5,6,7,8-tetrahydro-5,5,8,8-tetramethyl-2-naphthyl)-1-propenyl]-benzenephosphonate | $CH_2CH_2$ | $CH_3$ | $CH_3$ | H | $C(CH_3)=CH$ | $OCH_3$ | $OCH_3$ | 97-98 |
| 3 | Dibutyl (E)-4-[2-(5,6,7,8-tetrahydro-5,5,8,8-tetramethyl-2-naphthyl)-1-propenyl]-benzenephosphonate | $CH_2CH_2$ | $CH_3$ | $CH_3$ | H | $C(CH_3)=CH$ | $O-n-C_4H_9$ | $O-n-C_4H_9$ | 72-73 |
| 4 | Diethyl (E)-4-[2-(2,3-dihydro-1,1,2,3,3-pentamethyl-5(1H)-indenyl)-1-propenyl]-benzenephosphonate | $CH(CH_3)_2$ | $CH_3$ | $CH_3$ | H | $C(CH_3)=CH$ | $OC_2H_5$ | $OC_2H_5$ | 84-85 |
| 5 | Ethyl (E)-4-[2-(5,6,7,8-tetrahydro-5,5,8,8-tetramethyl-2-naphthyl)-1-propenyl]-phenyl-phenylphosphinate | $CH_2CH_2$ | $CH_3$ | $CH_3$ | H | $C(CH_3)=CH$ | $OC_2H_5$ | $C_6H_5$ | 101.5-103.5 |
| 6 | Ethyl (E)-4-[2-(5,6,7,8-tetrahydro-5,5,8,8-tetramethyl-2-naphthyl-1-propenyl]-phenyl-methylphosphinate | $CH_2CH_2$ | $CH_3$ | $CH_3$ | H | $C(CH_3)=CH$ | $OC_2H_5$ | $CH_3$ | 119-120 |

EXAMPLE 7 diethyl (E)-4-[(5,6,7,8-tetrahydro-5,5,8,8-tetramethyl-2-naphthyl)-ethynyl]-benzenephosphonate 4 g (19 millimoles) of 2-ethynyl-5,6,7,8-tetrahydro-5,5,8,8-tetramethylnaphthalene, 5 g (17 millimoles) of diethyl 4-bromobenzenephosphanate, 17 ml of triethylamine, 2.6 mg of bis-(triphenylphosphine)-palladium(II) chloride, 8.5 mg of copper(I) iodide and 17 mg of triphenylphosphine in 5 ml of dimethylformamide were refluxed for 50 minutes. The mixture was then allowed to cool, poured onto water and extracted with ether. The ether phase was washed with water, dried over Na₂SO₄ and evaporated down. The residue was recrystallized twice from heptane to give 2.6 g (33%) of the title compound of melting point 93°–95° C.

EXAMPLE 8

Diethyl (E)-4-[2-(5,6,7,8-tetrahydro-5,5,8,8-tetramethyl2-naphthyl)-1-ethenyl]-benzenephosphonate A solution of 22 g (53 millimoles) of diethyl 4diethylphosphonomethylbenzenephosphonate in 100 ml of dimethyl sulfoxide was added dropwise to a suspension of 1.8 g (64 millimoles) of sodium hydride in 50 ml of dry dimethyl sulfoxide at room temperature. Stirring was continued for 1 hour, after which a solution of 8.7 g (40 millimoles) of 2-formyl-5,6,7,8-tetrahydro-5,5,8,8-tetramethylnaphthalene in 75 ml of dimethyl sulfoxide was added dropwise. Stirring was continued for 16 hours at room temperature and the mixture was poured onto water, acidified with 2N hydrochloric acid and extracted three times with ether. The combined organic phases were washed twice with water and twice with saturated sodium chloride solution, dried over sodium sulfate and evaporated down. The residue was purified by column chromatography (silica gel; heptane/0.55 - 10% ethyl acetate) to give 5.5 g of the title compound of melting point 83°–84° C.

EXAMPLE 9

(E)-4-[2-(5,6,7,8-tetrahydro-5,5,8,8-tetramethyl-2-naphthyl)-1-propenyl]-benzenephosphonic acid 2 g (4.5 millimoles) of diethyl (E)-4-[2(5,6,7,8-tetrahydro-5,5,8,8-tetramethyl-2-naphthyl)-1propenyl]-benzenephosphonate, 1.86 g (18 millimoles) of sodium bromide and 3 g (27 millimoles) of trimethylchlorosilane in 10 ml of acetonitrile were stirred for 3 hours at 40° C. The mixture was then allowed to cool and was filtered, and the filtrate was evaporated down. The oil which remained was stirred for 30 minutes with water at room temperature and then extracted with ether, and the organic phase was washed with water, dried over sodium sulfate and evaporated down. Recrystallization of the residue from ethyl acetate gave 1.1 g of the title compound of melting point 208°–209° C.

EXAMPLE 10

Monoethyl (E)-4-[2-(5,6,7,8-tetrahydro-5,5,8,8-tetramethyl-2-naphthyl)-1-propenyl]-benzenephosphonate 1 g (2.3 millimoles) of diethyl (E)-4-[2(5,6,7,8-tetrahydro-5,5,8,8-tetramethyl-2-naphthyl)-1propenyl]-benzenephosphonate in a mixture of 8.9 ml of methanol and 5.9 ml of 10N NaOH were refluxed for 30 minutes. After the mixture had been cooled, the resulting precipitate was filtered off under suction and dried. It was then dissolved again in water and the solution was acidified with 2N HCl. The precipitate was filtered off under suction and dried to give 0.6 g of the title compound of melting point 165°–166° C.

We claim:

1. An arylphosphorus derivative of the formula

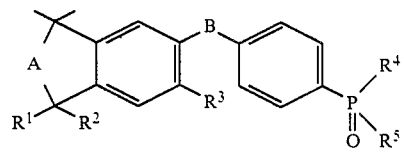

wherein A is an ethylene radical, B is a —CR⁶=CH— or —C≡C— group, R¹ and R² are each methyl, R³ is hydrogen and R⁴ and R⁵ are each —OR⁷, R⁶ is hydrogen or methyl, and R⁷ is hydrogen or a C₁₋₄ alkyl group and physiologically tolerated salts thereof.

2. The arylphosphorus derivative of claim 1, wherein B is —CR⁶=CH—.

3. The arylphosphorus derivative of claim 1, wherein B is —CR⁶=CH—.

4. The arylphosphorus derivative of claim 1, wherein R⁶ is hydrogen.

5. The arylphosphorus derivative of claim 1, wherein R⁶ is methyl.

6. The arylphosphorus derivative of claim 1, wherein R7 is hydrogen.

7. The arylphosphorus derivative of claim 1, wherein R⁷ is C₁₋₄ alkyl.

* * * * *